United States Patent [19]

Merchant et al.

[11] Patent Number: 5,807,247
[45] Date of Patent: Sep. 15, 1998

[54] METHOD AND APPARATUS FOR FACILITATING COMPATIBILITY BETWEEN PULSE OXIMETERS AND SENSOR PROBES

[75] Inventors: Adnan I. Merchant, Fremont; K. L. Venkatachalam, Palo Alto; Michael E. Fein, Mountain View, all of Calif.

[73] Assignee: Nellcor Puritan Bennett Incorporated, Pleasanton, Calif.

[21] Appl. No.: 575,256

[22] Filed: Dec. 20, 1995

[51] Int. Cl.⁶ ................................................ A61B 5/00
[52] U.S. Cl. ........................... 600/310; 600/322; 600/323
[58] Field of Search .............................. 128/633, 664–7; 356/39–41; 73/1 R; 324/601; 439/909; 600/310, 322, 323

[56] References Cited

U.S. PATENT DOCUMENTS

| | | | |
|---|---|---|---|
| 4,621,643 | 11/1986 | New, Jr. et al. | 128/633 |
| 4,700,708 | 10/1987 | New, Jr. et al. | 128/633 |
| 4,770,179 | 9/1988 | New, Jr. et al. | 128/664 |
| 5,048,524 | 9/1991 | Bailey | 128/643 |
| 5,259,381 | 11/1993 | Cheung et al. | 128/633 |
| 5,267,562 | 12/1993 | Ukawa et al. | 128/633 |

*Primary Examiner*—Jennifer Bahr
*Assistant Examiner*—Bryan K. Yarnell
*Attorney, Agent, or Firm*—Townsend and Townsend and Crew LLP

[57] ABSTRACT

A sensor probe operable to transmit light of a first wavelength for scattering by a tissue sample is described for use with a pulse oximeter designed to operate with another type of sensor probe which transmits light of a second wavelength. The sensor probe includes at least one source of light for transmitting light of the first wavelength for scattering and/or absorption by the tissue sample. At least one detector is included for detecting light of the first wavelength affected by the tissue sample and generating a signal in response thereto. An encoder in the sensor probe transforms the signal to a form which may be employed by the oximeter.

22 Claims, 8 Drawing Sheets

METHOD AND APPARATUS FOR FACILITATING COMPATIBILITY BETWEEN PULSE OXIMETERS AND SENSOR PROBES

BACKGROUND OF THE INVENTION

The present invention relates generally to the field of pulse oximetry. Specifically, the invention described herein relates to methods and apparatus for facilitating the use of a sensor probe from one manufacturer with the pulse oximeter of another.

Currently available pulse oximetry systems employ two or more wavelengths of light to estimate the oxygen saturation of hemoglobin in arterial blood, hereinafter referred to as saturation. For example, in a system manufactured by the assignee, Nellcor Incorporated, the two wavelengths employed are near 660 nm (red) and 900 nm (infrared). The two wavelengths are alternately transmitted through blood perfused tissue by LEDs in a sensor probe which is attached to the tissue sample (e.g., finger) in some manner. The light is modulated in the tissue by the changing blood volume. The modulated light is received after being scattered by the tissue by a detector such as, for example, a photo diode, which produces current in proportion to the intensity of the received light.

The output waveform of the detector is then amplified, filtered, and demultiplexed into separate red and infrared (IR) waveforms which represent the change in blood volume in the monitored tissue (i.e., plethysmograms or pleths). Each pleth is then digitized and subjected to a series of calculations, one of which results in the calculation of the so-called "ratio of ratios" value for each heart beat. The ratio of ratios, or R, is defined as:

$$R = \frac{\log\left(\frac{AC_{red}}{DC_{red}}\right)}{\log\left(\frac{AC_{IR}}{DC_{IR}}\right)} \quad (1)$$

where "log" refers to the natural logarithm and $AC_{red}$ = the AC current due to red LED
$DC_{red}$ = the DC current due to red LED
$AC_{IR}$ = the AC current due to IR LED
$DC_{IR}$ = the DC current due to IR LED Examples of pulse oximetry systems are described in commonly assigned U.S. Pat. No. 4,802,486; No. 5,078,136; and No. 5,368,026, the entire specifications of which are incorporated herein by reference.

The ratio of ratios, R, is related to saturation, S, via an empirically derived equation which includes blood extinction coefficients corresponding to the specific combination of wavelengths employed. This relationship defines a family of curves, S=f(R), each of which represents the relationship between saturation and R for a particular combination of wavelengths. Thus, the accuracy with which such a system calculates saturation is dependent, at least in part, upon the use of blood extinction coefficients to transform R which correspond to the actual wavelengths of light emitted by the LEDs in the sensor probe. Use of the wrong coefficients could result in large errors in the saturation value which, in turn, could have undesirable consequences with regard to the diagnosis and treatment of patients being monitored by a pulse oximetry system.

According to one technique for ensuring that a pulse oximeter employs the proper blood extinction coefficients, the coefficients are determined by the oximeter with reference to the wavelengths being transmitted by the probe. The sensor probe includes a means for generating an encoded signal which is indicative of the combination of wavelengths being transmitted by the sensor's LEDs. The oximeter receives the encoded signal and determines the proper extinction coefficients based on the encoded signal as specified by a table stored in the oximeter. This avoids the need to recalibrate an oximeter to match the transmission characteristics of a particular probe. The means for generating the encoded signal may be, for example, an electrical impedance element such as a resistor, the value of which corresponds to the combination of wavelengths of the LEDs. Examples of such a sensor/oximeter combinations are described in commonly assigned U.S. Pat. No. 4,621,643 for CALIBRATED OPTICAL OXIMETER PROBE, issued on Nov. 11, 1986, U.S. Pat. No. 4,700,708 for CALIBRATED OPTICAL OXIMETER PROBE, issued on Oct. 20, 1987, and U.S. Pat. No. 4,770,179 for CALIBRATED OPTICAL OXIMETER PROBE, issued on Sep. 13, 1988, the entire disclosures of which are all incorporated herein by reference.

There are occasions in every medical institution when the availability of properly functioning monitoring equipment becomes an issue. For example, medical personnel may encounter emergency situations in which a non-functioning oximeter sensor probe must be replaced quickly. If a sensor probe from the same manufacturer is not available, it obviously would be desirable to be able to use available sensor probes from another manufacturer. However, as discussed above, the oximeter would need to select different extinction coefficients to correspond to the wavelengths of the LEDs of the new probe. Unfortunately, the solution presented above only applies to situations in which the replacement probe and the oximeter are from the same manufacturer, i.e., where the oximeter "recognizes" and correctly interprets the calibration impedance of the sensor probe.

Figure 1:
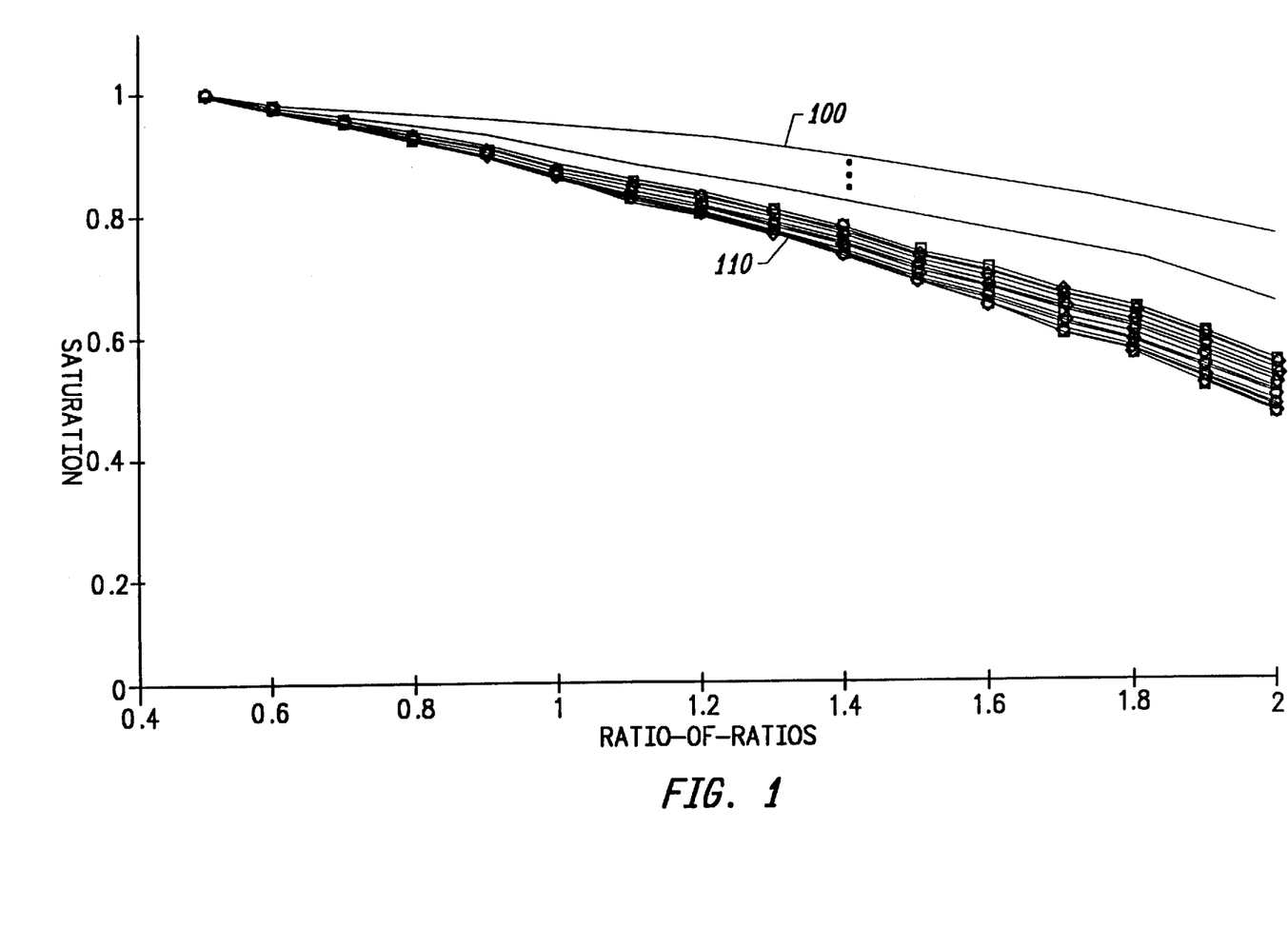
FIG. 1 depicts families of curves relating saturation to the ratio of ratios for two different pulse oximeters.

FIG. 1 shows two families of hypothetical calibration curves 100 and 110 which are similar to the curves used in two commercially available pulse oximeters from different manufacturers. Each calibration curve represents the relationship between the ratio of ratios and saturation (as calculated by the pulse oximeter) for a particular combination of red and IR wavelengths (as indicated by specific calibration impedances). Or more generally, each calibration curve represents the relationship between a calculated value derived from the scattered light data and saturation, where the calculated value may be R as defined above, or may be some other value if the particular oximeter uses an algorithm which does not specifically calculate R. Each combination of wavelengths corresponds to a particular calibration impedance. For example, resistor values may range from 19.6 kΩ to 39.2 kΩ for the oximeter corresponding to curves 110. As discussed above, these resistor values in the sensor probes indicate to the corresponding oximeter which extinction coefficients should be used to calculate saturation. It is common for calibration curves of one manufacturer not to overlap those of another manufacturer when the two manufacturers use probes having different wavelength combinations. It is evident from FIG. 1 that, unless a particular oximeter is reprogrammed to recognize the wavelength combinations of another manufacturer's probe and to employ the appropriate extinction coefficients, the saturation values calculated by one of the oximeters using probes from the other manufacturer could have unacceptable error levels.

It is therefore evident that a need exists for a method and apparatus by which sensor probes and oximeters from different manufacturers may be employed together to accurately measure the oxygen saturation of hemoglobin.

SUMMARY OF THE INVENTION

The present invention provides a method and apparatus for facilitating the use of a sensor probe from one manufacturer with a pulse oximeter from another. An apparatus is described for deriving the calibration curves of a particular pulse oximeter. The apparatus is connected to the pulse oximeter and simulates a sensor probe attached to a patient. The apparatus includes multiple LEDs which may be configured to accept drive signals from different types of pulse oximeters, and a detector diode which detects the light emitted by the LEDs. The output of the detector diode is manipulated so that the output of the apparatus simulates the detection of the light from the LEDs through a modulated blood volume. By changing the relative amplitudes of the signals, several values of the ratio of ratios are generated. For each value of the ratio of ratios, a saturation value is calculated by the pulse oximeter. In this way, a calibration curve for the pulse oximeter relating the ratio of ratios to saturation are generated. The entire family of calibration curves for the pulse oximeter are generated using the apparatus of the invention by repeating the single curve generation for different combinations of wavelengths.

Once the calibration curves for two different oximeters are known, a transformation function is derived which transforms the calibration curves of the first oximeter to approximate those of the second, i.e., the curves of the first are "mapped" onto the curves of the second. The transformation function is employed with a sensor probe designed to be used with the first oximeter to transform the output of the sensor probe so that it may also be used with the second oximeter. The circuitry which performs the transformation function resides in different places according to specific embodiments of the invention.

Thus, according to the invention, apparatus and method are described for providing compatibility between a meter and a sensor probe. The sensor probe includes at least one source of light and is operable to transmit light of a first wavelength for scattering and/or absorption by a tissue sample and to generate a first probe signal in response thereto. Typically, the light is detected after passing through the tissue sample, i.e., transillumination, or after being back-scattered from the tissue sample, i.e., reflectance. The meter is operable to receive a meter signal representative of light of a second wavelength affected by the tissue sample and to calculate a blood parameter therefrom using coefficients based at least in part on a value of the second wavelength. The invention comprises a signal transformer which manipulates the first probe signal thereby generating a transformed signal which has a predetermined mathematical relationship to the first probe signal. The transformed signal is then used by the meter to calculate the blood parameter using the coefficients based at least in part on the value of the second wavelength. According to specific embodiments, an encoded signal communicates a coded signal appropriate for wavelengths used by the probe, from the sensor probe, the coded signal being changed such that the coded signal received by the meter is appropriate so that the meter employs the appropriate coefficients to calculate the blood parameter.

The invention described herein may be configured in a variety of ways as set forth below in the detailed descriptions of various specific embodiments. For example, the signal transformer may be included as part of the sensor probe thereby making the sensor probe compatible with more than one type of meter. Alternatively, the signal transformer may be included as part of the meter thereby making the meter compatible with more than one type of sensor probe. Finally, the signal transformer may be part of an adapter module between the sensor probe and the meter.

According to various specific embodiments of the invention, the sensor probe comprises an oximetry probe, the meter comprises a pulse oximeter, the blood parameter comprises oxygen saturation of arterial hemoglobin, and the at least one source of light comprises red and infrared light emitting diodes. In a more specific embodiment, the red and infrared light emitting diodes transmit a first combination of wavelengths of light, and the coefficients are representative of a second combination of wavelengths. In this embodiment, the signal transformer manipulates the probe signal(s) (which can be any combination of the red signal, infrared signal, and a calculated signal which is obtained by manipulating and combining the red and infrared signals) such that accuracy of the blood parameter calculated by the meter using the transformed signal is greater than if the blood parameter were calculated using the first signal.

According to another specific embodiment, translation circuitry is included for providing electrical compatibility between the sensor probe and the meter.

Various specific embodiments of the invention employ different transformation functions by which any one of the probe signals are manipulated. According to a first embodiment, the probe signal is multiplied by a constant. According to a second embodiment, the probe signal is multiplied by a first constant to form a product and a second constant is added to the product. According to another embodiment in which the meter employs an intermediate parameter to calculate the blood parameter, processing circuitry calculates the intermediate parameter from the red and infrared signals and derives a transformation function therefrom by which the signal transformer then manipulates any one of the probe signals.

In some embodiments, calibration code circuitry is included for transmitting a desired calibration code to the meter thereby selecting the coefficients for calculation of the blood parameter.

According to some embodiments in which the signal transformer is not included in the meter, power circuitry is included which couples to the power terminals of the meter (e.g., LED drive terminals) so as to divert power to the signal transformer for generating the transformed signal. In a more specific embodiment, the power terminals provide −1.5 volts for driving the at least one source of light and the power circuitry converts the −1.5 volts to 5 volts for use by the signal transformer.

A further understanding of the nature and advantages of the present invention may be realized by reference to the remaining portions of the specification and the drawings.

DESCRIPTION OF THE PREFERRED EMBODIMENT

For two oximeters A and B designed to be used with sensor probes A and B, respectively, it is theoretically possible to map the calibration curves of one system onto those of the other by a transformation function of the general form $$R_B = f(R_A) \quad (2)$$

where $R_B$ represents the ratio of ratios for a signal stream from sensor probe B, and $R_A$ represents the ratio of ratios for a signal stream from sensor probe A. The transformation function $f(R_A)$ transforms the signal stream from sensor probe A in such a way as to make oximeter B compute and display the correct saturation value. The choice of transformation function $f(R_A)$ for a particular pair of oximetry systems A and B depends upon the calibration curves of the two oximeters and the level of precision with which it is desired to map the curves of oximeter A onto those of oximeter B. In the equation given above for the ratio of ratios, R, any one of the four terms may be manipulated to produce any desired value of R for a given signal stream. Thus, if an appropriate multiplication factor (e.g., as described with respect to the first embodiment) is introduced to one of the terms of R as generated by a particular sensor probe, and electrical compatibility is provided, the sensor probe may be employed with that selected pulse oximeter of another manufacturer.

Figure 2A:
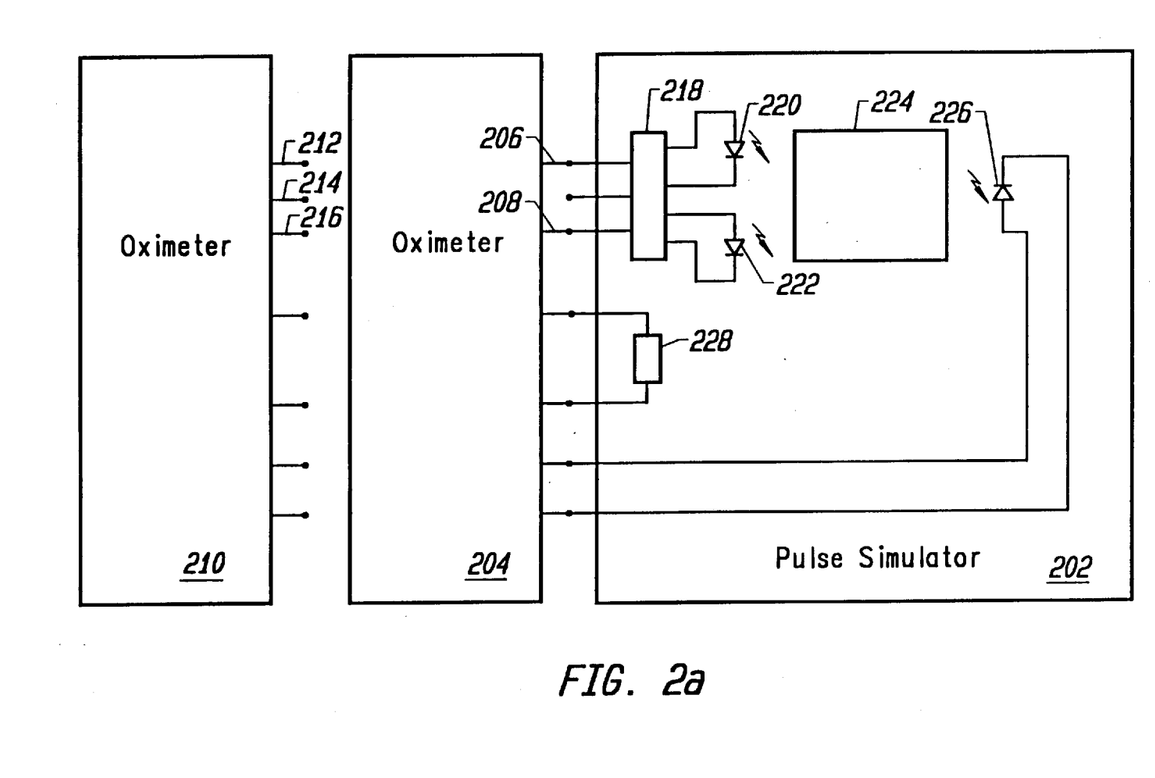
FIG. 2a is a block diagram of an apparatus for deriving calibration curves according to a specific embodiment of the invention.
Figure 2B:
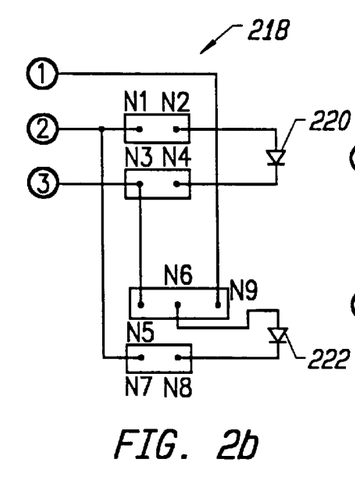
FIG. 2b is a detail of the block diagram of FIG. 2a according to a more specific embodiment.
Figure 2C:
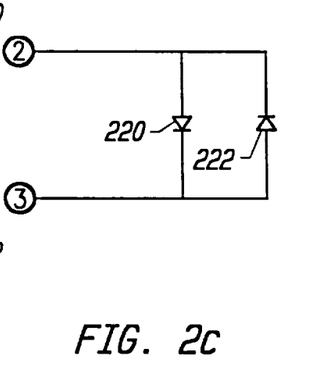
FIG. 2c is a diagram of a first configuration of LEDs.
Figure 2D:
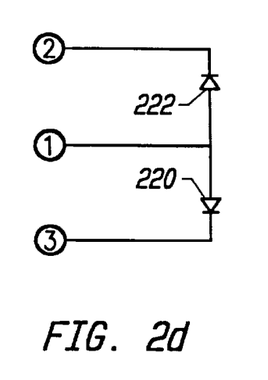
FIG. 2d is a diagram of a second configuration of LEDs.

FIG. 2a is a block diagram of an apparatus for deriving the calibration curves of a pulse oximeter. A pulse simulator 202 generates signals corresponding to a particular combination of red and infrared waveforms which are then transmitted to a first pulse oximeter 204 having known calibration coefficients. A wide variety of signal generators may be employed to perform this function as long as electrical compatibility between pulse simulator 202 and oximeter 204 is provided. In the embodiment shown in FIG. 2a, the first oximeter 204 is shown having two LED drive leads 206 and 208 while a second oximeter 210 has three LED drive leads 212, 214 and 216. Pulse simulator 202 employs switch circuitry 218 to provide compatibility between the drive configuration of the particular oximeter and red and infrared LEDs 220 and 222. In a specific embodiment, switch circuitry 218 is as shown in FIG. 2b. Using connections N1–N2, N3–N4, N5–N6 and N7–N8, LEDs 220 and 222 may be configured for two-wire LED drive as shown in FIG. 2c. Using connections N3–N4, N7–N8 and N6–N9, LEDs 220 and 222 may be configured for three-wire LED drive as shown in FIG. 2d.

Referring again to FIG. 2a, signal processing circuitry 224 manipulates signals representative of the light received from LEDs 220 and 222 so that the signal transmitted from detector diode 226 to the oximeter simulates the detection of red and infrared energy through a modulated blood volume. Pulse simulator 202 also includes an impedance element 228 for communicating a particular combination of red and infrared wavelengths to the pulse oximeter. The impedance of element 228 is variable and may be manipulated to communicate different combinations of wavelengths to the pulse oximeter for the purpose of deriving the entire family of calibration curves as described below.

Oximeter 204 calculates and displays a saturation value for the waveform combination. Because the calibration coefficients of oximeter 204 are known, a corresponding value of the ratio of ratios, R, may be calculated from the displayed saturation value. By selectively manipulating the signals, a range of saturation values and corresponding R values are generated, thereby yielding a calibration curve for the particular wavelength combination. This process is repeated for each set of signals representative of different combinations of red and infrared wavelengths (by manipulation of element 228) such that a family of calibration curves such as those shown in FIG. 1 is generated. The same sets of signals may then be transmitted to the second pulse oximeter 210 for which the calibration coefficients are not known. Because values of R are now known for the range of input signals for each wavelength combination, calibration curves may be derived for oximeter 210 by correlating each known value of R with an observed saturation value registered by oximeter 210 in response to the input signals.

It should be noted that the described method of deriving a set of calibration curves for a particular oximeter is not dependent on the actual algorithms employed by that oximeter to calculate saturation. As is true with many natural phenomena, many different mathematical approaches may be employed to calculate the same result. What is important is that the waveforms used properly simulate physiological waveforms which would be produced by actual oximeter sensors, and that the oximeters are known to compute oxygen saturation from these waveforms. For example, according to a specific embodiment of the invention, the first oximeter employs the internal mathematical variable R to characterize the relationship between red and infrared waveforms, and the second oximeter calculates saturation for a set of waveforms which correspond to a particular value of R, although the intermediate value R may or may not be used by the second oximeter at any point to describe the waveforms.

Figure 3:
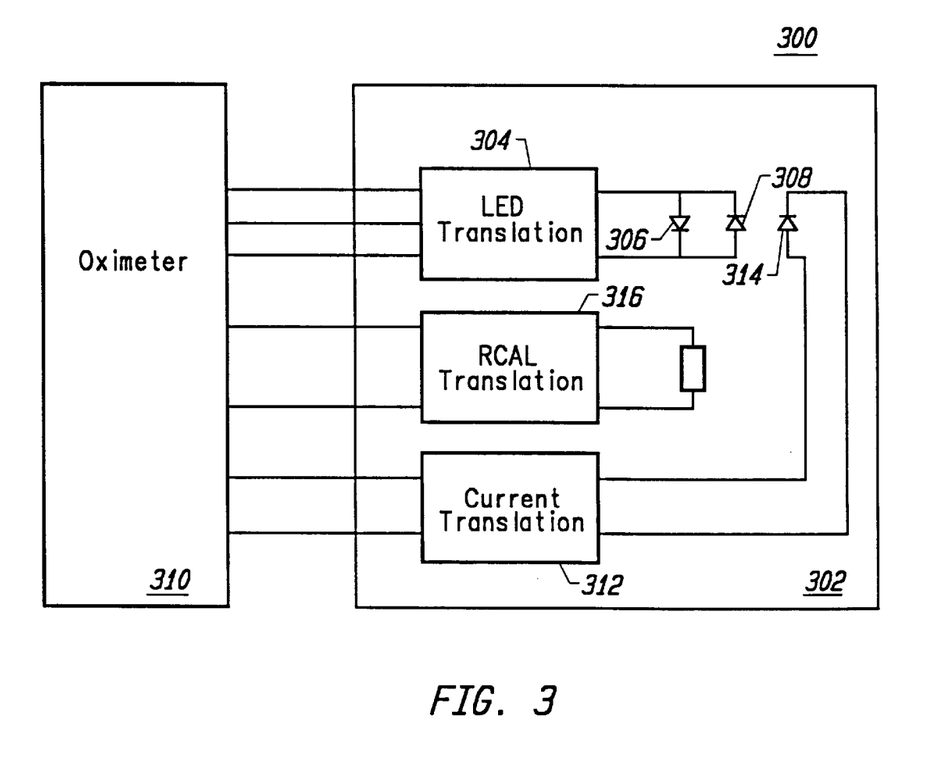
FIG. 3 is a block diagram of a pulse oximetry system employing a sensor probe designed according to a specific embodiment of the invention.

FIG. 3 is a block diagram of a pulse oximetry system 300 employing a sensor probe 302 designed according to a specific embodiment of the invention. Sensor probe 302 includes LED translation circuitry 304 which allows the user to configure LEDs 306 and 308 in a variety of ways to provide electrical and physical compatibility with pulse oximeter 310. In the embodiment of FIG. 3, LEDs 306 and 308 are shown configured for two-wire LED drive and oximeter 310 as a three-wire configuration oximeter. It will be understood that other embodiments of the invention have a sensor probe with its LEDs configured for three-wire LED drive for use with a two-wire configuration oximeter. A specific embodiment of LED translation circuitry 304 is described above with reference to FIG. 2b. Other specific embodiments of LED translation circuitry 304 are described in commonly assigned, copending U.S. Pat. application Ser. No. 08/575,336 for OPTICAL OXIMETER PROBE ADAPTER, the entire specification of which is incorporated herein by reference. In that application, an adapter is described which actively connects a two-wire LED oximeter probe configuration (e.g., FIG. 2c) to a monitor designed to use a three-wire LED probe, and a three-wire LED probe configuration (e.g., FIG. 2d) to a monitor designed to use a two-wire LED probe. This is done actively, with the drive signals from the oximeter monitor providing a control signal for switching the adapter connections. In specific embodiments, the adapter connections are made with diodes, transistors, or other active and passive devices. It will be understood that electrical compatibility between oximeter 310 and LEDs 306 and 308 may be provided in a variety of ways and is not limited to the configuration schemes discussed herein.

Referring to FIG. 3, when current translation circuitry 312 senses current from red LED 306, it applies a transformation function $f(R_A)$ to the current from detector diode 314 which corresponds to the time-invariant (DC) portion of the transmittance at the wavelength of red LED 306. According to one embodiment this is done via a voltage-controlled current amplifier. As discussed above, this transformation function allows oximeter 310, which is designed to be used with another type of probe, to calculate correct saturation values with the combination of LED wavelengths in sensor probe 302. It will be understood that, while in the specific embodiment described herein, the transformation function $f(R_A)$ is applied to the DC current of the detector which corresponds to the red LED, another appropriate transformation may be applied to either the time-varying or time-invariant current corresponding to either the red or infrared transmittance, or any combination thereof, to achieve the same result. According to a specific embodiment of the invention, the transformation function $f(R_A)$ simply multiplies the current from the detector diode by "1" thereby enabling sensor probe 302 to be used with a pulse oximeter made originally to be used with sensor like sensor 302. According to other embodiments, the current translation circuitry is either bypassed or disabled for this purpose.

Sensor probe 302 also transmits a probe ID signal to oximeter 310 via RCAL measurement circuitry 316 which instructs the oximeter to select a predetermined specific calibration curve appropriate for the transformation. Any of the calibration curves of oximeter 310 may be chosen by sending the appropriate signal, e.g., selecting the appropriate impedance value for monitors designed to receive an encoded signal based on impedance. The main criterion for selecting a particular calibration curve should be the minimization of the transformation error when mapping the calibration curves of one system onto another.

Figure 4:
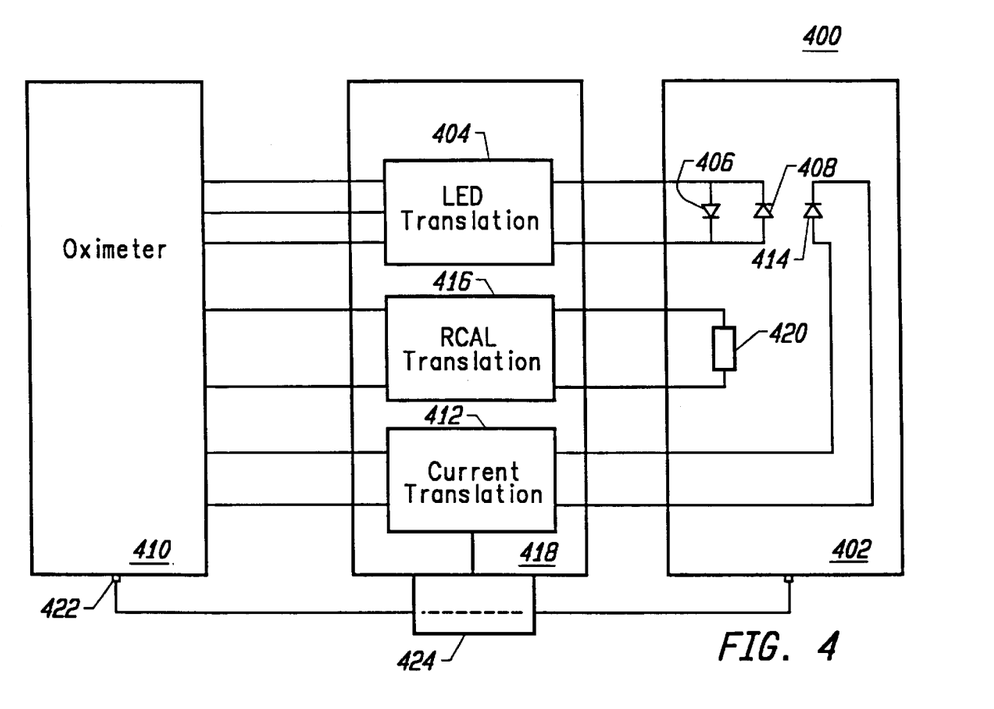
FIG. 4 is a block diagram of a pulse oximetry system employing an adapter module designed according to a specific embodiment of the invention.

Another specific embodiment of the invention is shown in FIG. 4. The operation of oximetry system 400 is similar to that of system 300 of FIG. 3 with corresponding components operating substantially as described above. However, in this embodiment, LED and current translation circuitry 404 and 412 are contained in adapter module 418 which is separate from and disposed between oximeter 410 and sensor probe 402. Once again, even though the embodiment of FIG. 4 shows adapter module 418 adapting a two-wire sensor probe to a three-wire oximeter, it will be understood that other embodiments of the adapter module are operable to adapt a three-wire probe to a two-wire oximeter. In a more specific embodiment, adapter module 418 also includes RCAL translation circuitry 416 which receives the RCAL signal from an impedance element 420 in sensor probe 402, modifies it, and transmits the modified RCAL signal to oximeter 410, thereby selecting a desired calibration curve.

According to another more specific embodiment, power circuitry in adapter module 418 "steals" power from a power terminal on oximeter 410 to provide power to the various translation circuits in module 418. In the embodiment of FIG. 4, power terminal 422 provide −1.5 volts to sensor probe 402. Power circuitry 424 taps into the −1.5 volts and converts a portion of the current available from the −1.5 volts source to +5 volts and −5 volts for use by current translation circuitry 412. It will be understood that similar circuitry may be employed to power the translation circuitry in sensor probe 302 of FIG. 3.

Figure 5:
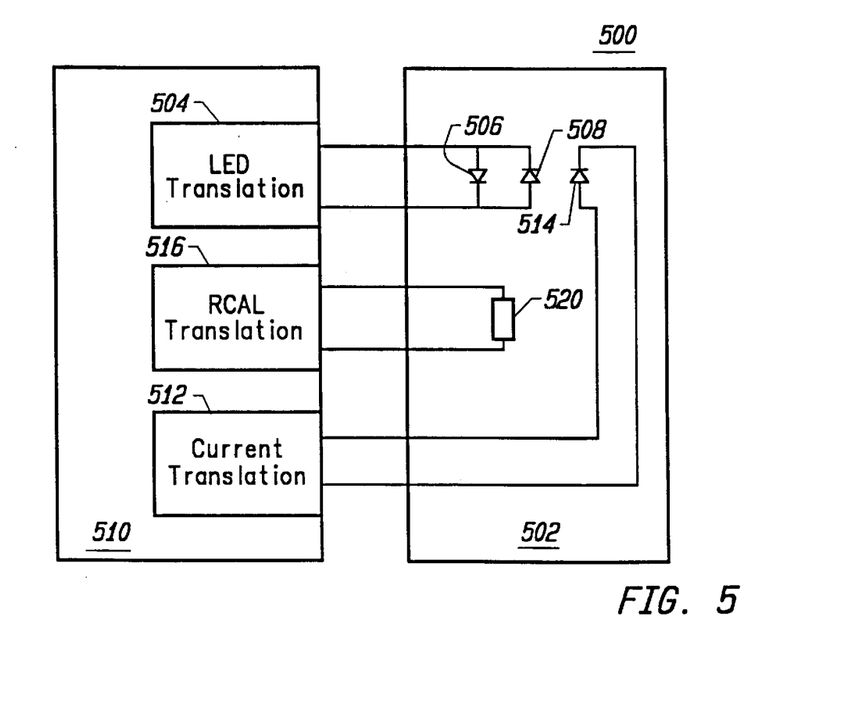
FIG. 5 is a block diagram of a pulse oximetry system employing an oximeter designed according to a specific embodiment of the invention.

Another specific embodiment of the invention is shown in FIG. 5. The operation of system 500 is similar to that of systems 300 and 400 of FIGS. 3 and 4 with corresponding components operating substantially as described above. However, in this embodiment, LED and current translation circuitry 504 and 512 are contained in pulse oximeter 510. As with the embodiments of FIGS. 3 and 4, even though FIG. 5 shows a two-wire sensor probe 502 being used with oximeter 510, it will be understood that oximeter 510 is operable to be used with a three-wire probe. That is, through the use of translation circuitry 504, 512 and 516, oximeter 510 is compatible with both two and three-wire sensor probes from different manufacturers.

Figure 6:
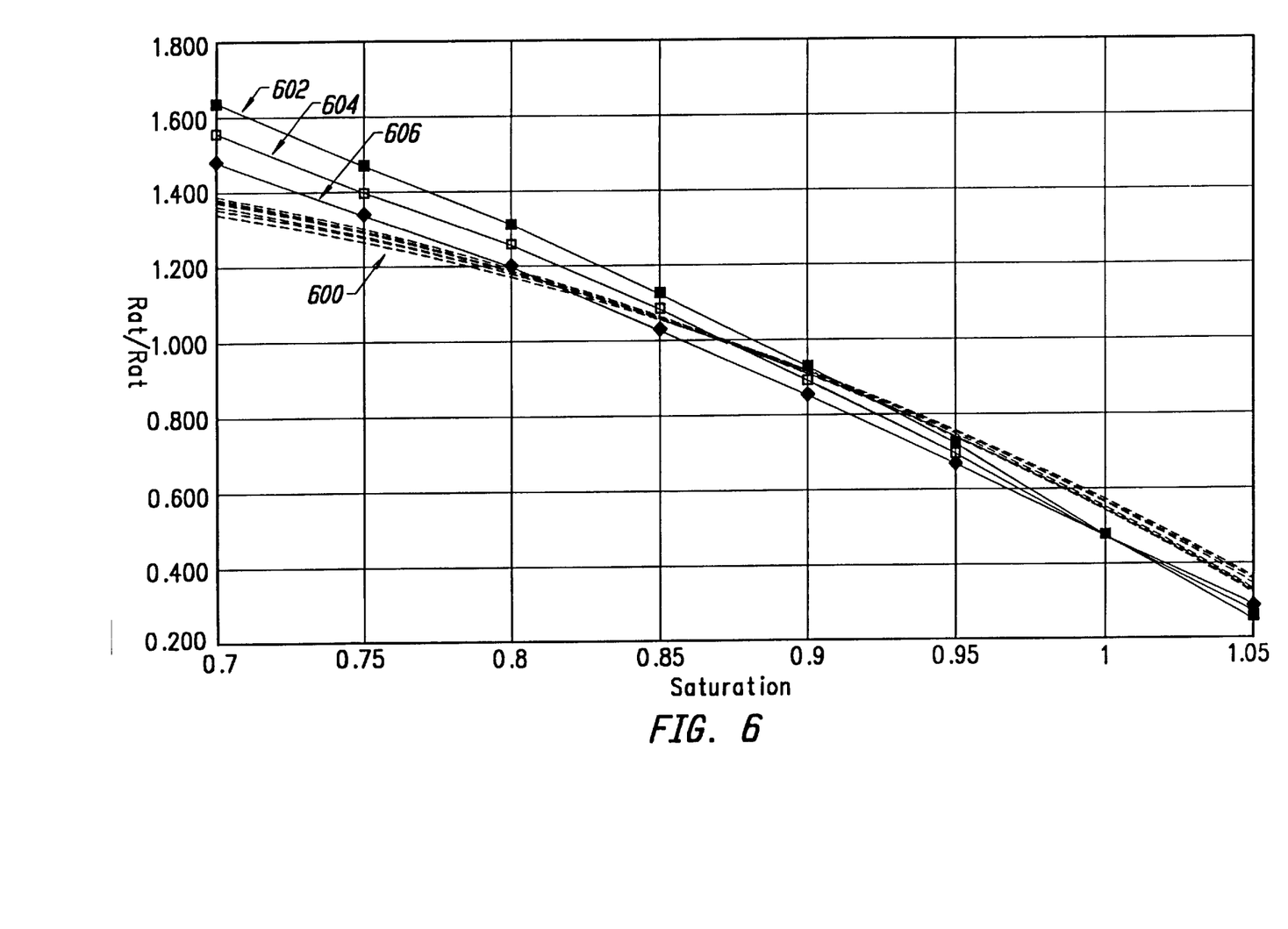
FIG. 6 is an illustration of the transformation of a family of curves corresponding to a first oximetry system to approximate a family of curves corresponding to a second oximetry system according to a first embodiment of the invention.

As mentioned above, transformation function $f(R_A)$ may be a variety of functions depending upon how closely the calibration curves from one oximeter are to be matched to those of another. FIG. 6 is an illustration of a family of curves of a first oximeter corresponding to curves 100 of FIG. 1 which has been transformed to approximate the family of curves of a second oximeter corresponding to curves 110 of FIG. 1 according to a specific embodiment of the invention. In this embodiment, $f(R_A)=m\lambda \cdot R_A$, where $m\lambda$ is a constant for each wavelength combination in sensor probes for the first oximeter. As can be seen in FIG. 6, the family of calibration curves 600 from oximeter A (which corresponds to curves 100 in FIG. 1 as transformed) quite closely approximates the family of curves from oximeter B (curves 110 of FIG. 1) as represented by upper and lower boundary curves 602 and 606, and intermediate curve 604. In this embodiment, equations (1) and (2) reduce to $$R_B = m_\lambda \cdot \frac{\log\left(\frac{AC_{red}}{DC_{red}}\right)_A}{\log\left(\frac{AC_{IR}}{DC_{IR}}\right)_A} \qquad (3)$$

As discussed above $m\lambda$ may be used to modify any one of the terms of equation (1) to effect the transformation. According to a preferred embodiment, each unique wavelength combination has a unique $m\lambda$, and the wavelength combination used by each probe is communicated to the current translation circuitry via a calibration signal, e.g., RCAL signal. Alternatively, even though $m\lambda$ is preferably a unique value for each wavelength combination, a fixed value of $m\lambda$ may be chosen which maps (approximately of course) all of the calibration curves from the first oximeter onto one curve from the second oximeter. The obvious advantage of selecting such a value of $m\lambda$ is that, in such an embodiment, the same current translation may be employed for sensor probes having different wavelength combinations, though reduced accuracy is a tradeoff.

Figure 7:
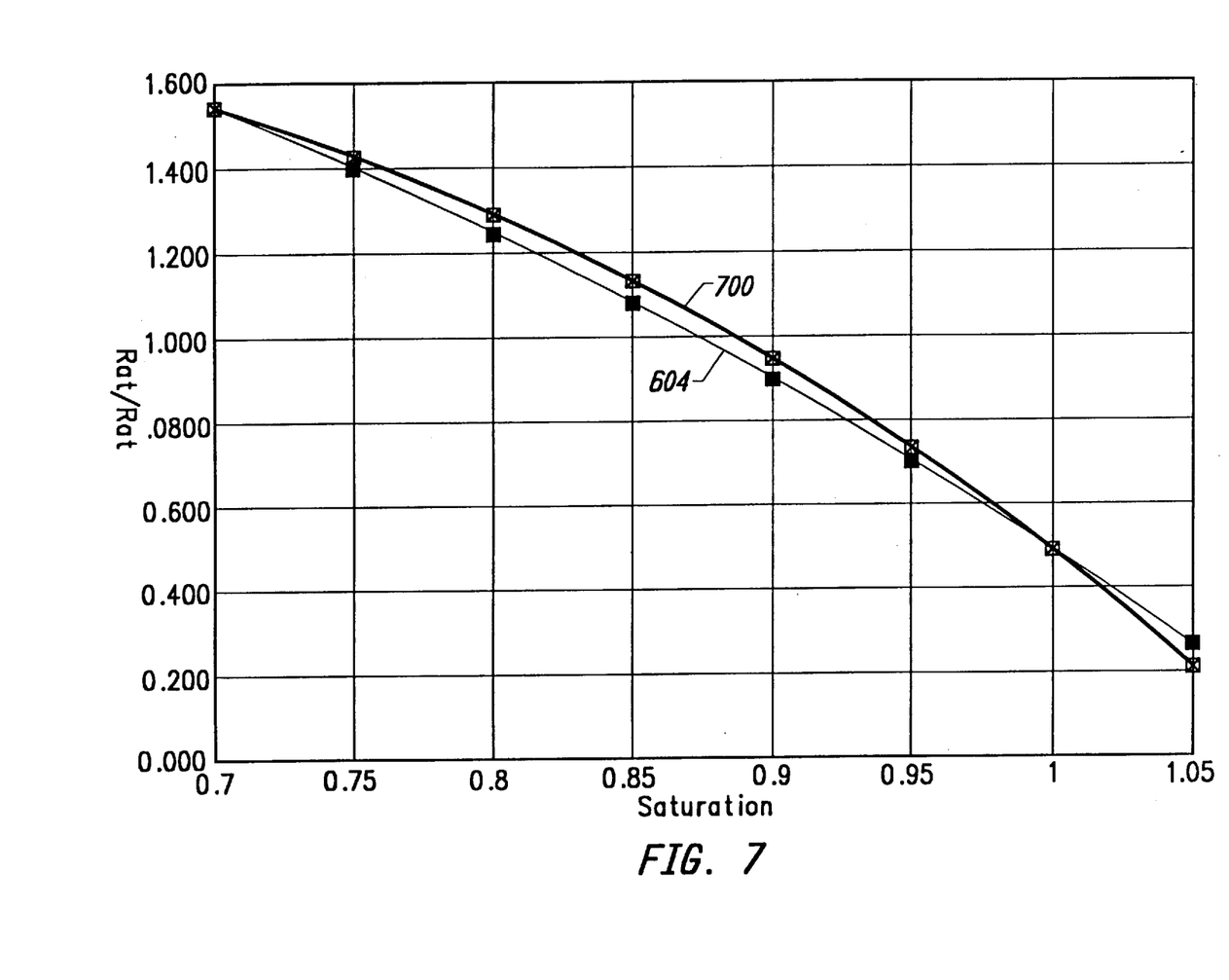
FIG. 7 is an illustration of the transformation of a family of curves corresponding to a first oximetry system to approximate a family of curves corresponding to a second oximetry system according to a second embodiment of the invention.

FIG. 7 is an illustration of a family of curves 700 corresponding to the first oximeter (A) of FIG. 1 which has been transformed to approximate calibration curve 604 (FIG. 6) of the second oximeter (B) according to another specific embodiment of the invention. In this embodiment, $f(R_A)=m\lambda \cdot R_A + b$, where $m\lambda$ and b are constants for each wavelength combination in sensor probes made for use with the first oximeter. In this embodiment, equations (1) and (2) reduce to $$R_B = m_\lambda \cdot \frac{\log\left(\frac{AC_{red}}{DC_{red}}\right)_A}{\log\left(\frac{AC_{IR}}{DC_{IR}}\right)_A} + b \tag{4}$$

This transformation function is obviously more difficult to implement than the simple constant of equation (3), but as can be seen in FIG. 7, a significant mapping improvement is realized.

Figure 8:
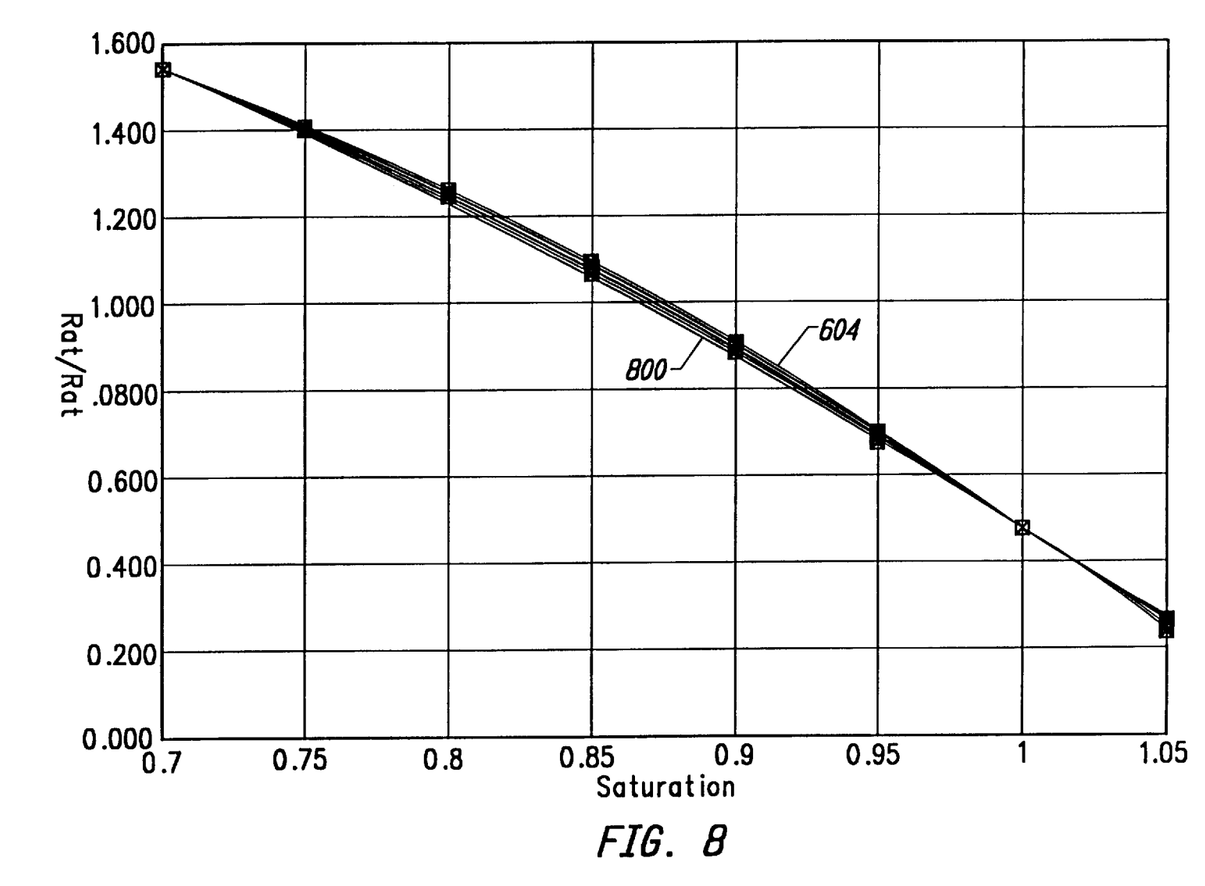
FIG. 8 is an illustration of the transformation of a family of curves corresponding to a first oximetry system to approximate a family of curves corresponding to a second oximetry system according to a third embodiment of the invention.

FIG. 8 is an illustration of a family of curves 800 corresponding to the first oximeter (A) of FIG. 1 which has been transformed to approximate single calibration curve 604 of the second oximeter (B) according to still another specific embodiment of the invention. In this embodiment, $f(R_A)=[m\lambda \cdot R_A+b] \cdot R_A$, where $m\lambda$ and b are constants for each wavelength combination in sensor probes made for use with the first oximeter.

$$R_B = \left[ m_\lambda \cdot \frac{\log\left(\frac{AC_{red}}{DC_{red}}\right)_A}{\log\left(\frac{AC_{IR}}{DC_{IR}}\right)_A} + b \right] \cdot \frac{\log\left(\frac{AC_{red}}{DC_{red}}\right)_A}{\log\left(\frac{AC_{IR}}{DC_{IR}}\right)_A} \tag{5}$$

This transformation function is even more difficult to implement than the function of equation (4), but the mapping improvement is such that calibration curve 604 is nearly indistinguishable from curves 800. Essentially, the more accurate the mapping desired, the more complicated and difficult to implement the transformation becomes.

In still a further embodiment, current translation circuitry 312 of FIG. 3 includes processing circuitry which actually calculates the ratio of ratios for the red and IR signal streams and determines an $f(R_A)$ which maps the calibration curve corresponding to the wavelength combination of sensor probe 302 onto a specifically selected calibration curve of pulse oximeter 310 (as selected by an appropriate impedance value). This transformation technique, while being the most difficult to implement, is also the most accurate in that the calibration curve of oximetry system A which corresponds to sensor probe 302 may be exactly mapped onto any one of the calibration curves of oximeter 310. It will be understood that this technique also may be employed with the embodiments of FIGS. 4 and 5.

Figure 9:
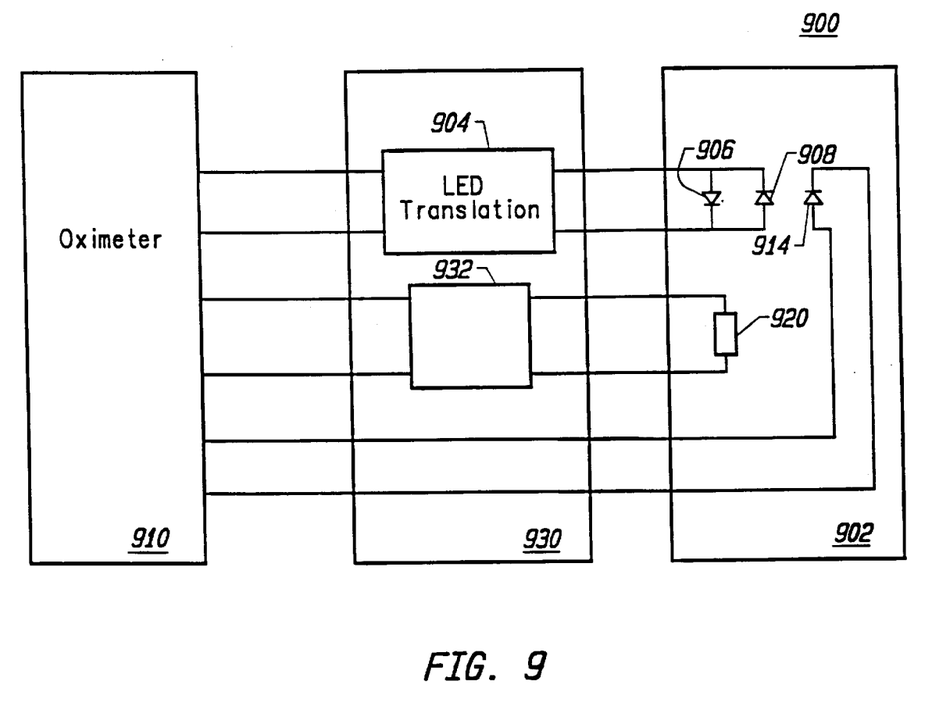
FIG. 9 is a block diagram illustrating another embodiment of the invention for facilitating compatibility between oximetry probes and pulse oximeters from different manufacturers.

Another approach to facilitating compatibility between oximetry probes and pulse oximeters of different manufacture is described with reference to FIG. 9. A probe adapter 930 is interposed between a standard oximetry probe 902 from one manufacturer and a pulse oximeter 910 from another, adapter 930 providing the necessary physical and electrical compatibility between probe 902 and oximeter 910 via LED translation circuitry 904 as described above, if required. Probe adapter 902 also disables calibration impedance element 920 of probe 902 via calibration disabling circuitry 932 which substitutes a specific impedance value therefor such that a particular calibration curve of the pulse oximeter 910 is always selected. Red and infrared LEDs 906 and 908 in oximetry probe 902 can be selected during manufacture of the sensor probe to always correspond to the combination of wavelengths indicated by the selected value of the calibration impedance.

While the invention has been particularly shown and described with reference to specific embodiments thereof, it will be understood by those skilled in the art that the foregoing and other changes in the form and details may be made therein without departing from the spirit or scope of the invention.

What is claimed is:

1. A sensor probe operable to transmit light of a first wavelength for scattering by a tissue sample and to generate a first probe signal in response thereto, the sensor probe being for use with a meter, the meter being operable to receive a meter signal representative of light of a second wavelength scattered by the tissue sample and to calculate a blood parameter from the meter signal using coefficients based at least in part on a value of the second wavelength, the sensor probe comprising:

at least one source of light for transmitting the light of the first wavelength for scattering by the tissue sample;

at least one detector for detecting the light of the first wavelength scattered by the tissue sample and generating the first probe signal in response thereto; and a signal transformer for manipulating the first probe signal thereby generating a transformed signal having a predetermined mathematical relationship to the first probe signal, the transformed signal being used by the meter to calculate the blood parameter using the coefficients based at least in part on the value of the second wavelength.

2. The sensor probe of claim 1 wherein the sensor probe comprises a pulse oximetry probe, the meter comprises a pulse oximeter, and the blood parameter comprises oxygen saturation of arterial hemoglobin, the at least one source of light comprising red and infrared light emitting diodes.

3. The sensor probe of claim 2 wherein the red and infrared light emitting diodes transmit a first combination of wavelengths of light, the first probe signal including any combination of a second probe signal generated by the first wavelength, a third probe signal generated by light of a third wavelength, and a calculated probe signal obtained by manipulating and combining the second and third probe signals, the transformer manipulating any combination of any of the probe signals to generate a desired number of transformed signals for use by the meter.

4. The sensor probe of claim 3 wherein the coefficients are based on a single wavelength value.

5. The sensor probe of claim 3 wherein the coefficients are based on a combination of wavelength values.

6. The sensor probe of claim 1 further comprising translation circuitry for providing electrical compatibility between the sensor probe and the meter.

7. The sensor probe of claim 1 wherein the signal transformer is operable to manipulate the first probe signal by multiplying the first probe signal by a constant.

8. The sensor probe of claim 1 wherein the signal transformer is operable to manipulate the first probe signal by multiplying the first probe signal by a first constant to form a product and adding a second constant to the product.

9. The sensor probe of claim 1 wherein the meter employs an intermediate parameter to calculate the blood parameter, the sensor probe further comprising processing circuitry for calculating the intermediate parameter from at least the first probe signal and deriving a transformation function therefrom by which the signal transformer manipulates at least one of the first probe signal and the intermediate parameter.

10. The sensor probe of claim 1 further comprising calibration code circuitry for transmitting a desired calibration code to the meter thereby selecting the coefficients based at least in part on a value of the second wavelength for calculation of the blood parameter.

11. The sensor probe of claim 1 wherein the meter comprises at least one power terminal for providing power to external circuitry of the probe, the sensor probe further comprising power circuitry for coupling to the at least one power terminal and diverting power from the external circuitry to provide power to the signal transformer for generating the transformed signal.

12. The sensor probe of claim 11 wherein the at least one power terminal provides a first voltage for driving the at least one source of light and the power circuitry, the sensor probe further comprising means for transforming the first voltage to a second voltage for use by the signal transformer.

13. A method for facilitating compatibility between a sensor probe operable to transmit light of a first wavelength for scattering by a tissue sample and to generate a first probe signal in response thereto, and a meter operable to receive a meter signal representative of light of a second wavelength scattered by the tissue sample and to calculate a blood parameter from the meter signal using coefficients based at least in part on a value of the second wavelength, the method comprising the steps of:

transmitting light of the first wavelength towards the tissue sample to be scattered thereby;

detecting light of the first wavelength scattered by the tissue sample;

generating the first probe signal in response to the detecting step;

manipulating the first probe signal, thereby generating a transformed signal having a predetermined mathematical relationship to the first probe signal, the transformed signal being used by the meter to calculate the blood parameter using the coefficients based at least in part on the value of the second wavelength.

14. The method of claim 13 wherein the first probe signal includes any combination of a second probe signal generated by the first wavelength, a third probe signal generated by light of a third wavelength, and a calculated probe signal obtained by manipulating and combining the second and third probe signals, the manipulating step comprising manipulating any combination of any of the probe signals to generate a desired number of transformed signals for use by the meter.

15. The method of claim 14 wherein the coefficients are based on a single wavelength value.

16. The method of claim 14 wherein the coefficients are based on a combination of wavelength values.

17. The method of claim 13 further comprising the step of providing electrical compatibility between the sensor probe and the meter.

18. The method of claim 13 wherein the manipulating step comprises multiplying the first probe signal by a constant.

19. The method of claim 13 wherein the manipulating step comprises multiplying the first probe signal by a first constant to form a product and adding a second constant to the product.

20. The method of claim 13 wherein the meter employs an intermediate parameter to calculate the blood parameter, the method further comprising the steps of calculating the intermediate parameter from at least the first probe signal and deriving a transformation function therefrom by which the signal transformer manipulates at least one of the first probe signal and the intermediate parameter.

21. The method of claim 13 further comprising the step of transmitting a desired calibration code to the meter thereby selecting the coefficients based at least in part on the value of the second wavelength for calculation of the blood parameter.

22. The method of claim 21 further comprising the steps of:

preventing transmittal of a first calibration code from the sensor probe to the meter; and generating the desired calibration code for transmittal to the meter in place of the first calibration code.

* * * * *